(12) United States Patent
Connors et al.

(10) Patent No.: US 11,730,846 B2
(45) Date of Patent: Aug. 22, 2023

(54) FRAGRANCE DIFFUSION COLLECTOR ASSEMBLY, EXCHANGEABLE FRAGRANCE CARTRIDGE, AND FRAGRANCE DIFFUSION SYSTEM AND METHOD

(71) Applicant: ScentAir Technologies, LLC, Charlotte, NC (US)

(72) Inventors: Daniel J. Connors, Nokomis, FL (US); Matthew L. Browne, Gastonia, NC (US); Logan T. Andres, Indian Trail, NC (US)

(73) Assignee: ScentAir Technologies, LLC, Charlotte, NC (US)

( * ) Notice: Subject to any disclaimer, the term of this patent is extended or adjusted under 35 U.S.C. 154(b) by 191 days.

(21) Appl. No.: 17/437,277

(22) PCT Filed: Mar. 12, 2020

(86) PCT No.: PCT/US2020/022317
§ 371 (c)(1),
(2) Date: Sep. 8, 2021

(87) PCT Pub. No.: WO2020/186018
PCT Pub. Date: Sep. 17, 2020

(65) Prior Publication Data
US 2022/0160924 A1    May 26, 2022

Related U.S. Application Data

(60) Provisional application No. 62/817,207, filed on Mar. 12, 2019.

(51) Int. Cl.
*A61L 9/14* (2006.01)
*B05B 15/30* (2018.01)
(Continued)

(52) U.S. Cl.
CPC .............. *A61L 9/14* (2013.01); *A61L 9/122* (2013.01); *B05B 7/0012* (2013.01);
(Continued)

(58) Field of Classification Search
None
See application file for complete search history.

(56) References Cited

U.S. PATENT DOCUMENTS

| | | |
|---|---|---|
| 2,119,643 A | 6/1938 | Mendl |
| 2,689,150 A | 9/1954 | Croce |
(Continued)

FOREIGN PATENT DOCUMENTS

WO    PCT/US20/22317    3/2020

*Primary Examiner* — Jelitza M Perez
(74) *Attorney, Agent, or Firm* — Schwartz Law Firm, P.C.

(57) ABSTRACT

A collector assembly is adapted for use in a fragrance diffusion system. The collector assembly incorporates a dual-thread collector base including an integrally-formed cartridge coupler and neck. The cartridge coupler has an internal screw thread designed for mating with a complementary external screw thread of a fragrance cartridge. The neck has an external screw thread which matches the internal screw thread of the cartridge coupler. An atomizing device including a flow nozzle is attached to the collector base and defines an internal air passage to an atomization chamber. An airblast through the internal passage of the nozzle creates a suction force drawing liquid fragrance from the cartridge through a vacuum tube and into the atomization chamber where the liquid fragrance is converted into droplets prior to discharging outwardly through a vapor port and into a vapor chamber inside the cartridge.

20 Claims, 11 Drawing Sheets

(51) Int. Cl.
 *A61L 9/12* (2006.01)
 *B05B 7/00* (2006.01)
 *B05B 7/24* (2006.01)

(52) U.S. Cl.
 CPC ............ *B05B 7/2429* (2013.01); *B05B 15/30* (2018.02); *A61L 2209/133* (2013.01); *A61L 2209/134* (2013.01)

(56) References Cited

U.S. PATENT DOCUMENTS

| | | |
|---|---|---|
| 3,752,590 A | 8/1973 | Frappe |
| 3,799,448 A | 3/1974 | Nozawa et al. |
| 7,913,933 B2 | 3/2011 | Van Roemburg |
| 8,695,896 B2 | 4/2014 | Tu |
| 9,211,357 B1 | 12/2015 | Li |
| 9,849,206 B1 | 12/2017 | Hsiao |
| 2007/0029475 A1 | 2/2007 | Hausmann et al. |
| 2011/0297275 A1 | 12/2011 | Farrar et al. |
| 2016/0263602 A1 | 9/2016 | Ivri |
| 2016/0339135 A1 | 11/2016 | Becker et al. |
| 2017/0036177 A1 | 2/2017 | Rosener et al. |
| 2017/0112956 A1 | 4/2017 | Sevy |
| 2017/0113237 A1 | 4/2017 | Scott et al. |
| 2018/0292058 A1 | 10/2018 | Li |

FRAGRANCE DIFFUSION COLLECTOR ASSEMBLY, EXCHANGEABLE FRAGRANCE CARTRIDGE, AND FRAGRANCE DIFFUSION SYSTEM AND METHOD

TECHNICAL FIELD AND BACKGROUND OF THE DISCLOSURE

The present disclosure relates broadly and generally to a fragrance diffusion collector assembly, exchangeable fragrance cartridge, and fragrance diffusion system and method. Examples of related assemblies, systems, and methods are disclosed in prior U.S. Pat. Nos. 7,651,077, 8,602, 396, 8,881,999, 8,857,735, 9,474,820, 9,446,162, 9,460,404, 9,715,223, 9,927,789, and 9,884,298 owned by the applicant, Scentair Technologies, LLC. The complete disclosures of these prior patents are incorporated herein by reference.

In exemplary embodiments, the present invention has application in a wide variety of environments and surroundings—both residential and commercial, and may enable manual on-demand and automated (e.g., programmed) scent delivery into targeted fragrance zones of 800 to 2000 square feet or more. For businesses, scent can trigger instant emotional connections with customers thereby promoting sales. Studies show that customers tend to perceive a scented space as being of better quality. Scent may also helps create a lasting first impression, evoke warm feelings of familiarity, improve mood, and create memorable experiences and associations in minds of customers. The right scent can encourage customers to shop and interact with products longer. Pleasant scents can also help customers feel relaxed, happy and ready to do business.

SUMMARY OF EXEMPLARY EMBODIMENTS

Various exemplary embodiments of the present disclosure are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

It is also noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

According to one exemplary embodiment, the present disclosure comprises an exchangeable fragrance cartridge (or "bottle") incorporating a collector assembly and adapted for use in a fragrance diffusion system. The term "fragrance cartridge" refers broadly herein to both the combined exchangeable fragrance cartridge and collector assembly, and to the exchangeable fragrance cartridge without the collector assembly—i.e., prior to attachment of the collector assembly. The exemplary collector assembly incorporates a dual-thread collector base including an integrally-formed cartridge coupler and neck. The cartridge coupler has an internal screw thread designed for mating with a complementary external screw thread of an exchangeable fragrance cartridge. The neck has an external screw thread matching the internal screw thread of the cartridge coupler, such that an outside diameter of the neck measured at an outermost thread is equal to an inside diameter of the cartridge coupler measured at a maximum depth of the internal screw thread. The term "matching" refers to male (external) and female (internal) screw threads of complementary design, such that the external screw thread of the neck would operatively mate with any other internally-threaded structure having a thread design comparable to the cartridge coupler, and the internal screw thread of the cartridge coupler would operatively mate with any other externally-threaded structure having a thread design comparable to the neck. In exemplary embodiments, the screw threads are straight threads.

An atomizing device comprises a flow nozzle attached to the collector base and defining an internal air passage. The air passage has a first open end adapted for communicating with a source of compressed air and a second open end extending into an atomization chamber formed with the collector base. The atomization chamber defines a vapor port adapted for communicating with an inside of the fragrance cartridge. The atomizing device further comprises an end wall sealing the atomization chamber on an output side of the collector base. An elongated vacuum tube is fluidly connected to the atomization chamber on a cartridge side of the collector base, and adapted for extending into a liquid fragrance stored inside the fragrance cartridge. The term "liquid fragrance" refers to any combination of essential oils, oil blends, aroma chemicals, water, diluents, and the like. An airblast through the internal passage of the nozzle creates a suction force drawing liquid fragrance from the cartridge through the vacuum tube and into the atomization chamber where the liquid fragrance is converted into droplets prior to discharging outwardly through the vapor port and into a vapor chamber inside the cartridge. At least one diffusion opening is formed in the collector base for enabling movement of fragrant vapor outwardly from the cartridge. In exemplary embodiments, the fragrant vapor may comprise particles 1/50th the size of aerosol.

According to another exemplary embodiment, the collector base includes a centrally formed open-end (open access) nozzle housing.

According to another exemplary embodiment, the nozzle housing has a cylindrical upper side wall, a reduced-diameter cylindrical lower side wall adjacent the upper side wall, and an inside annular shoulder located between the upper and lower side walls.

According to another exemplary embodiment, the atomizing device further comprises a mounting disk integrally formed with the nozzle intake and having a marginal edge portion affixed (e.g., welded) to the collector base along the annular shoulder of the nozzle housing.

According to another exemplary embodiment, the mounting disk comprises a protruding annular cartridge-side flange.

According to another exemplary embodiment, the lower cylindrical side wall of the nozzle housing is tapered to closely receive the cartridge-side flange of the mounting disk.

According to another exemplary embodiment, a perforated collector wall is located inside the collector base and extends between (and divides) the cartridge coupler and the neck.

According to another exemplary embodiment, the air passage through the nozzle tapers between the first and second open ends, and forms a constricted Venturi tip designed to blast airflow into the atomization chamber and from the atomization chamber through the vapor port.

According to another exemplary embodiment, the vacuum tube includes a fixed tube section integrally formed with the cartridge side of the collector base, and an elongated removable extension tube fluidly connected to the fixed tube section.

According to another exemplary embodiment, the nozzle comprises a tapered nipple adapted for fluidly connecting to the source of compressed air.

According to another exemplary embodiment, first and second spaced apart O-rings are located on the tapered nipple and function to fluidly seal the connection between the nozzle and the source of compressed air.

According to another exemplary embodiment, the internal and external screw threads of the collector base each comprise at least one continuous turn.

According to another exemplary embodiment, a removable closure cap has an internal screw thread designed for mating with the external thread of the neck of the collector base. The internal screw thread of the exemplary closure cap matches the internal screw thread of the cartridge coupler.

According to another exemplary embodiment, the dual-thread collector base is molded of a plastic material as a single homogenous unit and receives the atomizing device in an integrally-formed 2-piece collector assembly.

In another exemplary embodiment, the disclosure comprises a collector assembly adapted for use in an exchangeable fragrance cartridge of a fragrance diffusion system. The term "exchangeable" refers broadly herein to a fragrance cartridge which is removable, replaceable, disposable and/or refillable. The exemplary fragrance cartridge may offer up to 300 running hours of use, or 30 days installed in the fragrance diffusion system. The exemplary collector assembly comprises an integrated unit and is likewise removable and replaceable.

In yet another exemplary embodiment, the disclosure comprises fragrance diffusion system incorporating an exchangeable fragrance cartridge and the present collector assembly.

In yet another exemplary embodiment, the disclosure comprises a method for fragrancing air.

Applicant's prior U.S. Pat. No. 8,881,999 (the '999 Patent) incorporated by reference herein discloses a fragrance diffusion system and method. Some of the exemplary embodiments and operations of the present disclosure may be computer-implemented as described and illustrated in the '999 Patent. Specifically, the '999 Patent states that such implementation may occur in digital electronic circuitry, or in computer software, firmware, or hardware, or in combinations of one or more of them. Embodiments of the present disclosure can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, e.g., a machine-generated electrical, optical, or electromagnetic signal, which is generated to encode information for transmission to suitable receiver apparatus for execution by a data processing apparatus. The data processing apparatus may include the sensor, may be part of the sensor, may be a part of a system with the sensor, may be integrated within the system and/or sensor, may be part of receivers, transmitters, components and/or logic associated with the sensor or the receivers and/or transmitters, or any combination thereof. A computer storage medium can be, or be included in, a computer-readable storage device, a computer-readable storage substrate, a random or serial access memory array or device, or a combination of one or more of them. Moreover, while a computer storage medium itself is not a propagated signal, a computer storage medium can be a source or destination of computer program instructions encoded in an artificially generated propagated signal. The computer storage medium can also be, or be included in, one or more separate physical components or media (e.g., other storage devices). Some of the operations applicable in the present disclosure can be implemented as operations performed by a data processing apparatus on data stored on one or more computer-readable storage devices or received from other sources.

Various apparatuses, devices, and machines for processing data, may be used as a "data processing apparatus," including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows applicable in the present disclosure can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Devices suitable for storing computer program instructions and data include all forms of non volatile memory, media and memory devices, including by way of example semiconductor memory devices, e.g., EPROM, EEPROM, and flash memory devices; magnetic disks, e.g., internal hard disks. The processor and the memory can be supplemented by, or incorporated in, special purpose logic circuitry.

To provide for interaction with a user, embodiments of the present disclosure can be implemented on a computer having a display device, e.g., a CRT (cathode ray tube) or LCD (liquid crystal display) monitor, for displaying information to the user and an input device, such as a pointing device, a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

BRIEF DESCRIPTION OF THE DRAWINGS

Exemplary embodiments of the present disclosure will hereinafter be described in conjunction with the following drawing figures, wherein like numerals denote like elements, and wherein.

DESCRIPTION OF EXEMPLARY
EMBODIMENTS AND BEST MODE

The present invention is described more fully hereinafter with reference to the accompanying drawings, in which one or more exemplary embodiments of the invention are shown. Like numbers used herein refer to like elements throughout. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Figure 1:
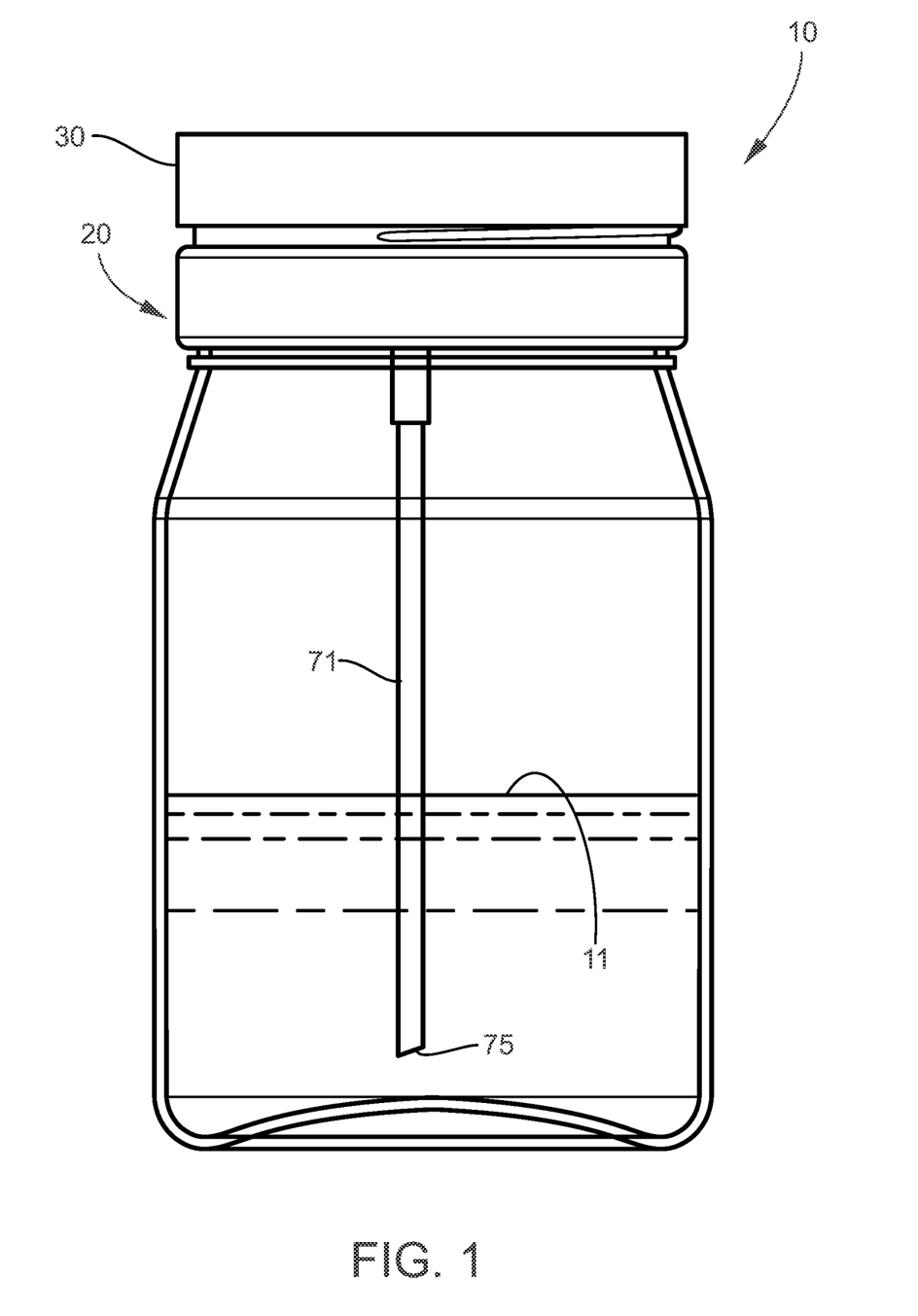
FIG. 1 is a side view of an exchangeable fragrance cartridge incorporating the present collector assembly according to one exemplary embodiment of the disclosure.
Figure 2:
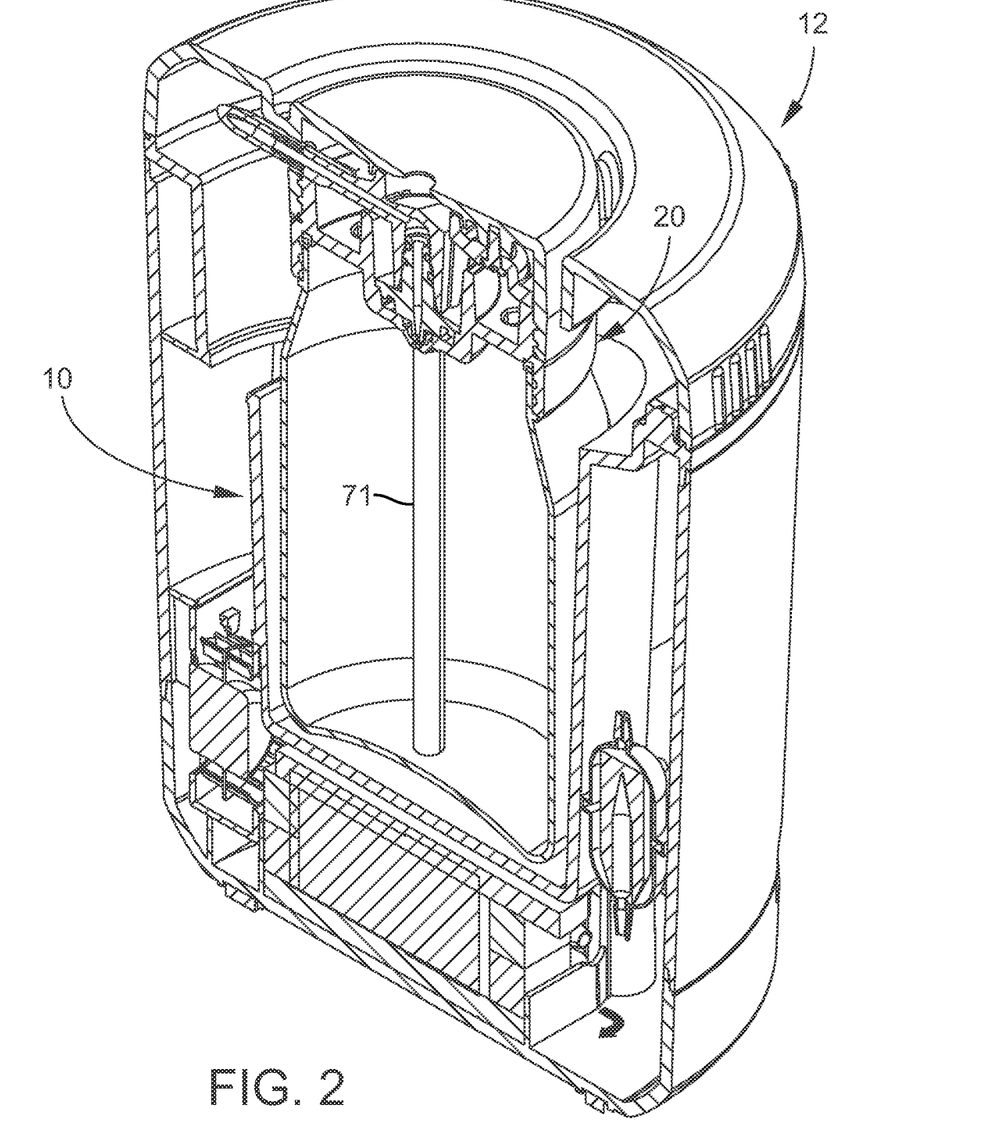
FIG. 2 is a cross-sectional view showing the exchangeable fragrance cartridge operatively mounted inside a fragrance diffusion system.

Referring now specifically to the drawings, an exchangeable fragrance cartridge according to one exemplary embodiment of the present disclosure is illustrated in FIGS. 1 and 2, and shown generally at broad reference numeral 10. The exemplary cartridge 10 stores a fragrance oil 11 and is designed for use in a fragrance diffusion system 12, such as disclosed in Applicant's prior U.S. patents incorporated herein by reference.

Figure 3:
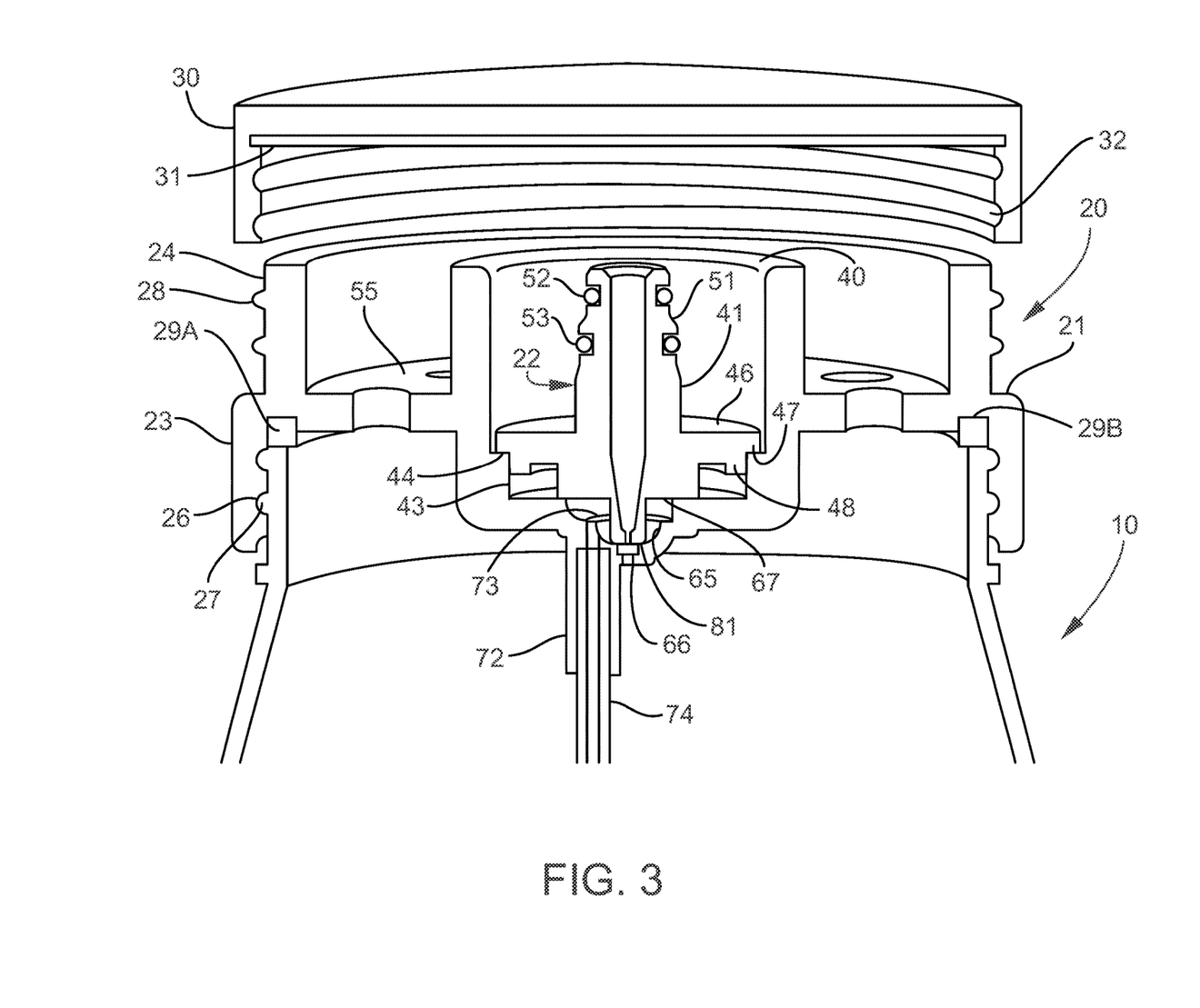
FIG. 3 is a fragmentary cross-sectional view of the exemplary fragrance cartridge with a closure cap of the cartridge removed.
Figure 4:
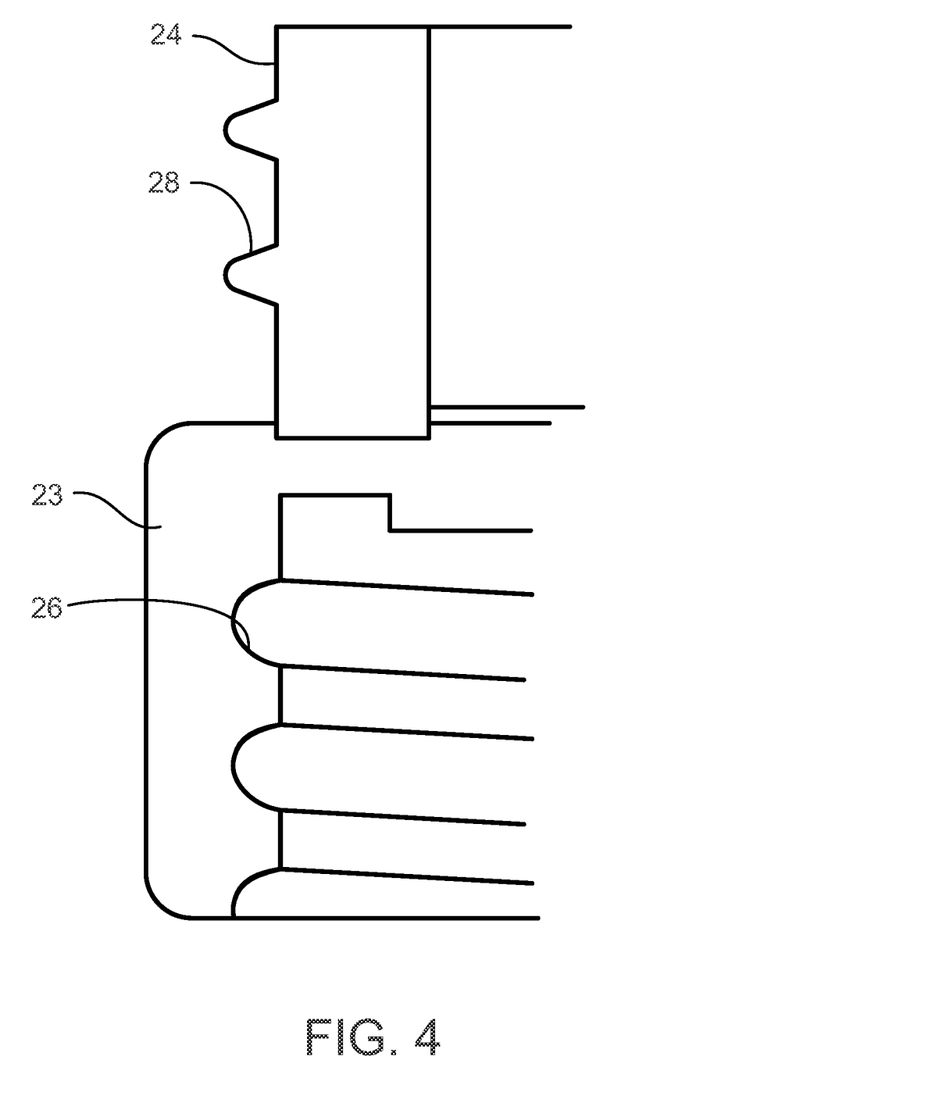
FIG. 4 is an enlarged fragmentary cross-sectional view of the collector base illustrating the matching male and female screw threads of the collector assembly.
Figure 5:
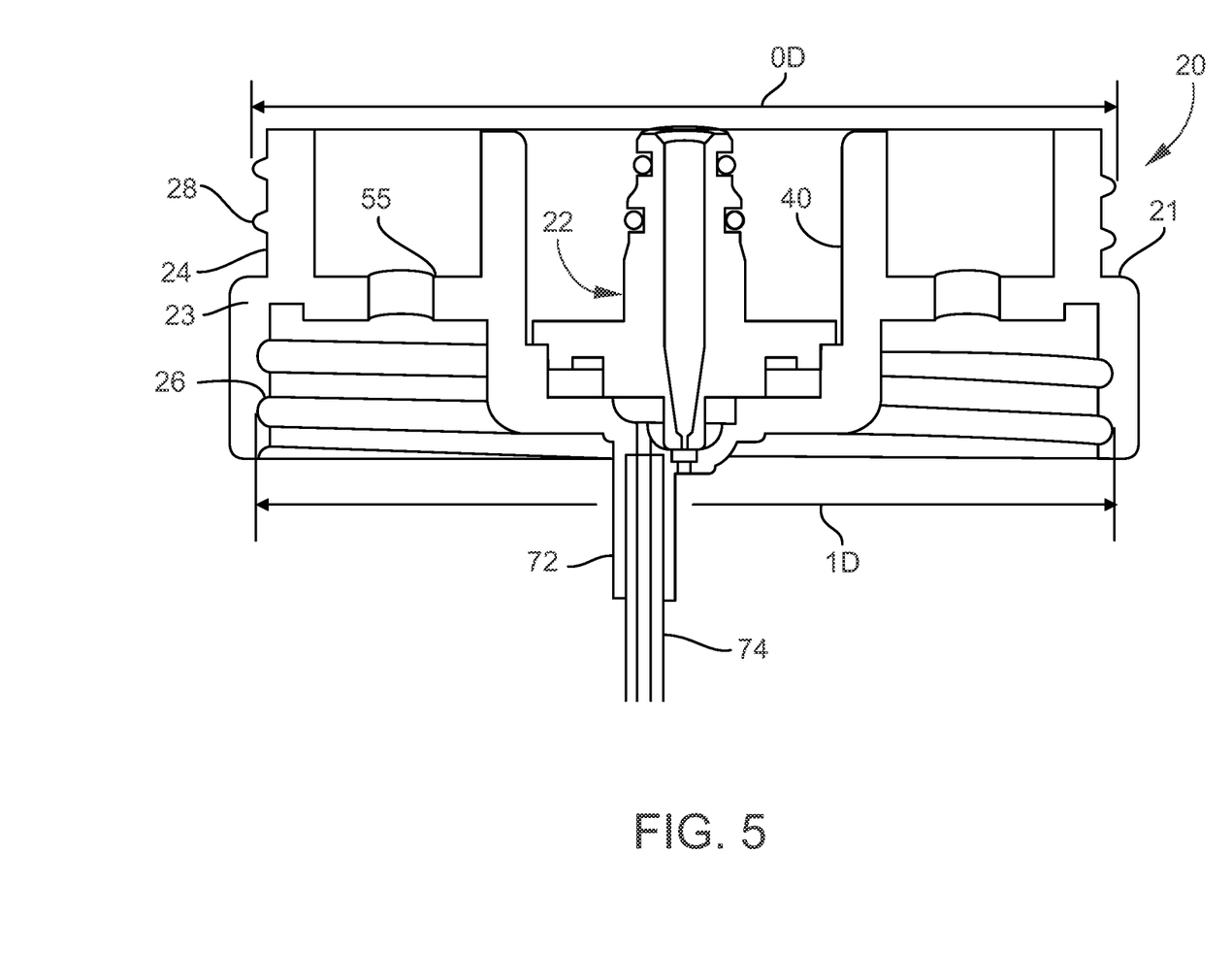
FIG. 5 is a further cross-sectional view of the exemplary collector assembly.

Referring to FIGS. 1 and 3, the present fragrance cartridge 10 incorporates a 2-piece collector assembly 20 comprising a dual-thread collector base 21 and an airblast venturi atomizing device 22 (or atomizing complex). The collector base 21 includes an integrally-molded cartridge coupler 23 and neck 24. The cartridge coupler 23 has an internal screw thread 26 which mates with a complementary external screw thread 27 of the fragrance cartridge 10. The neck 24 has an external screw thread 28 matching the internal screw thread 26 of the cartridge coupler 23, as best shown in FIGS. 3, 4 and 5, such that an outside diameter "OD" of the neck 24 measured at an outermost thread 28 is equal to an inside diameter "ID" of the cartridge coupler 23 measured at a maximum depth of the internal screw thread 26. See FIG. 5. For packaging, shipping and storage, the exchangeable fragrance cartridge 10 may further include a removable closure cap 30 comprising a chemical resistant liner 31 and an internal screw thread 32 designed for mating with the external thread 28 of the neck 24 of the collector base 21. In exemplary embodiments, the fragrance cartridge 10, cartridge coupler 23 and neck 24 of collector base 21, and closure cap 30 all have matching screw threads (or finishes)—e.g., identical 70/410 straight threads each with 1.5 turns. A square rubber gasket 29A may fit within a gasket channel 29B of the collector base 21 to further seal the threaded connection between the exchangeable fragrance cartridge 10 and collector assembly 20.

Figure 6:
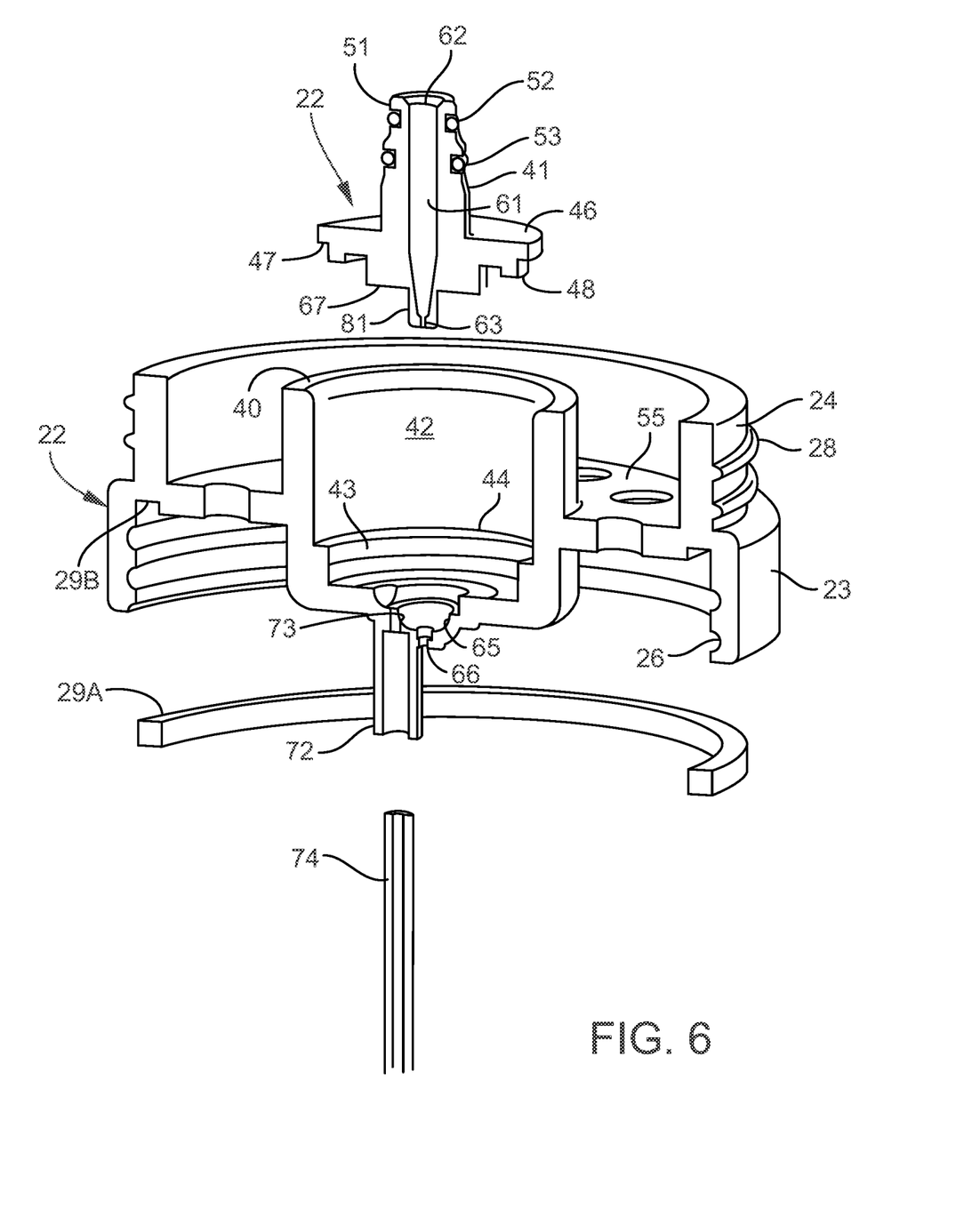
FIG. 6 is a cross-sectional view showing various parts of the collector assembly exploded away.
Figure 7:
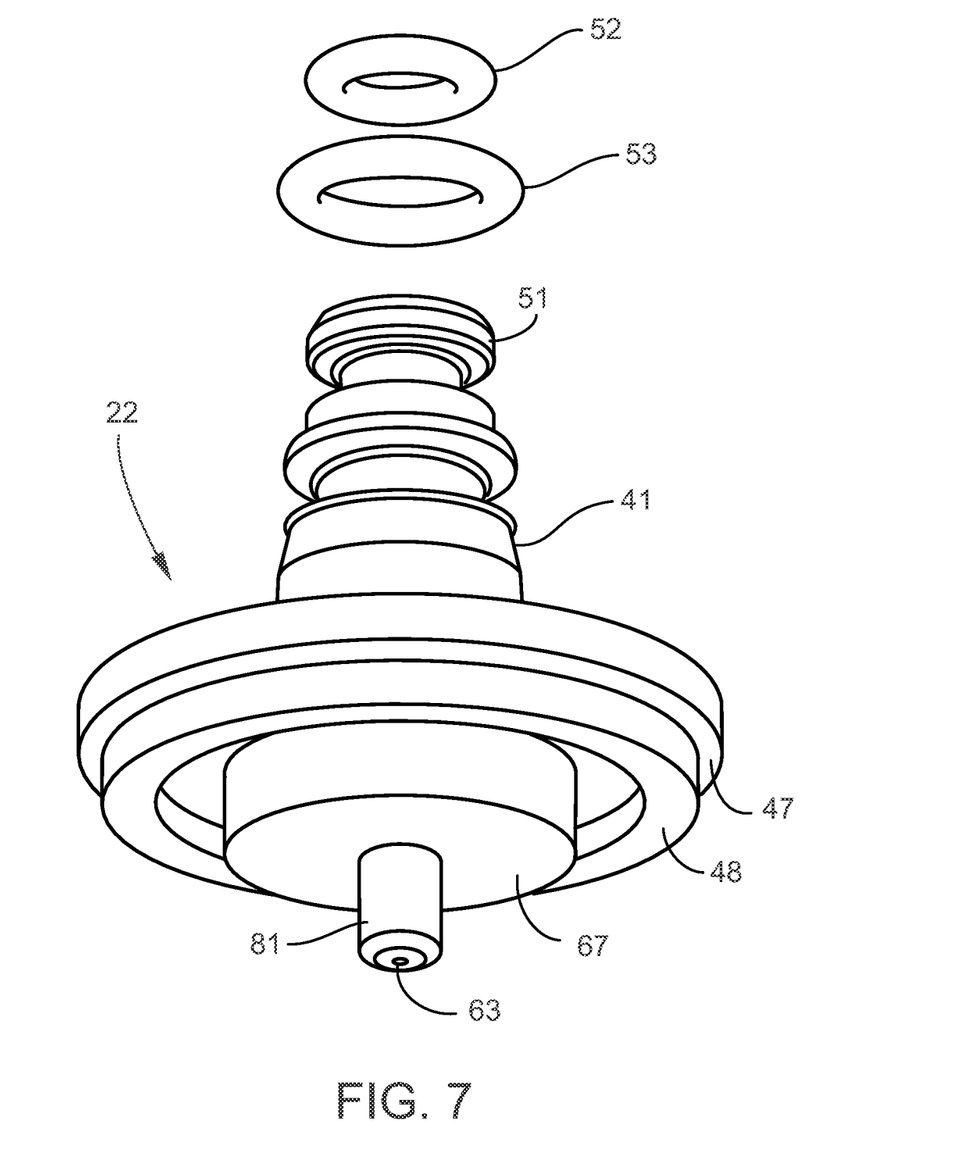
FIG. 7 is a perspective view of the atomizing device showing the O-rings exploded from the nozzle.
Figure 8:
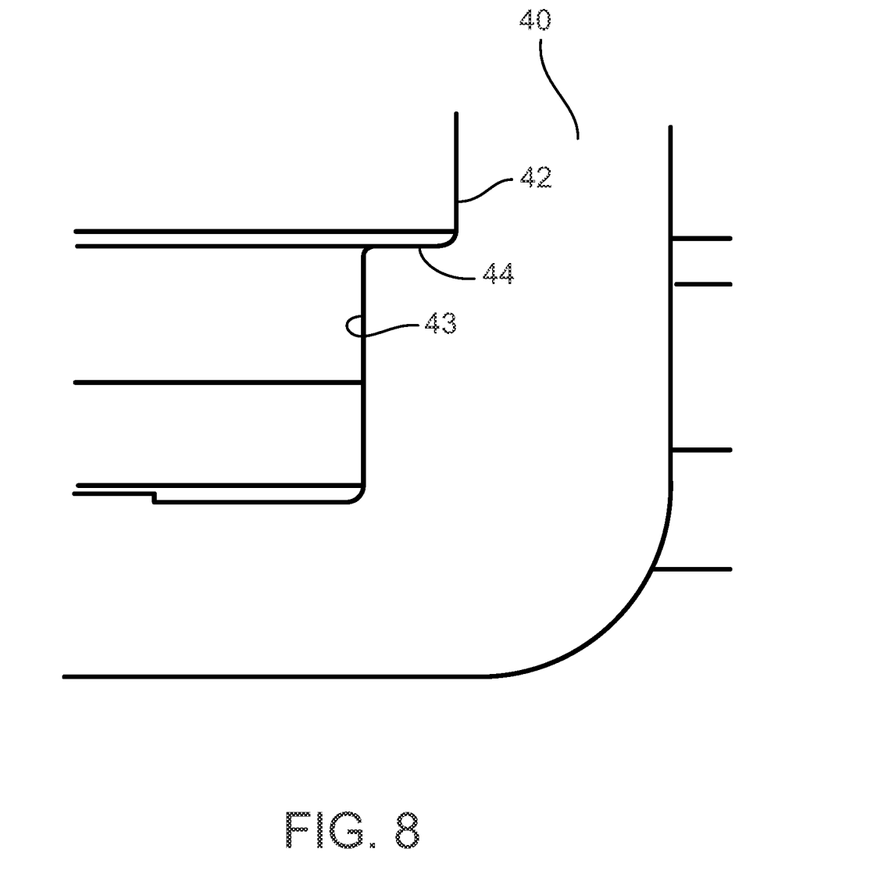
FIG. 8 is an enlarged fragmentary cross-sectional view of the collector base illustrating a slight tapering of the lower cylindrical wall of the nozzle housing.
Figure 9:
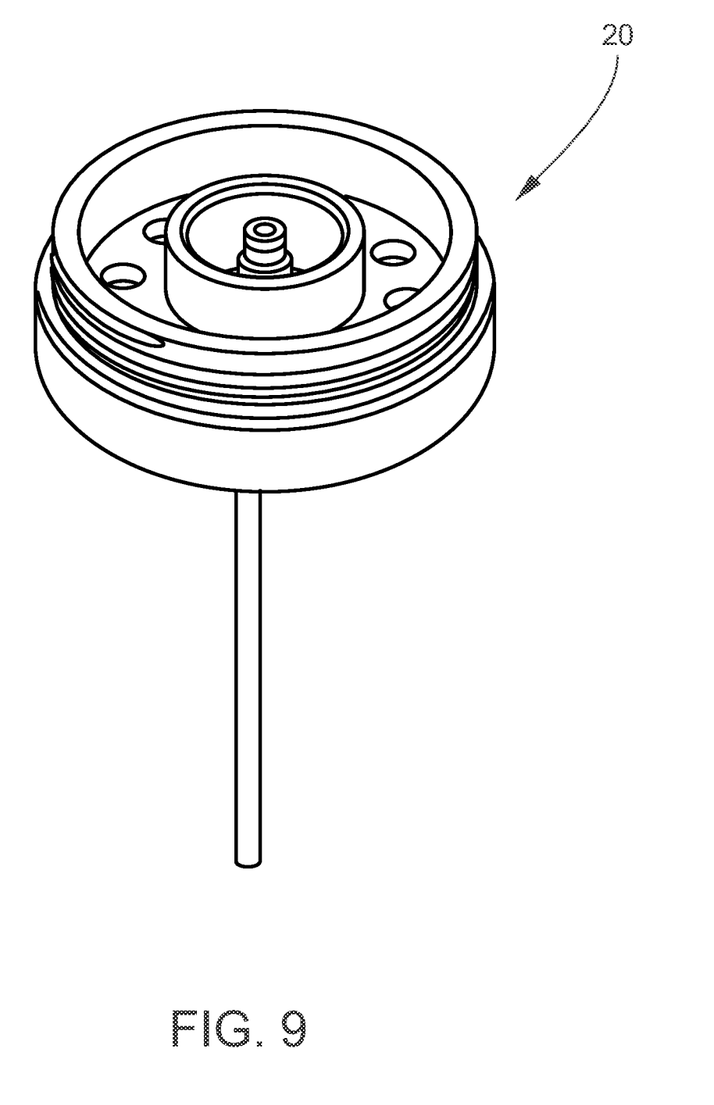
FIGS. 9 and 10 are further perspective views of the exemplary collector assembly.
Figure 10:
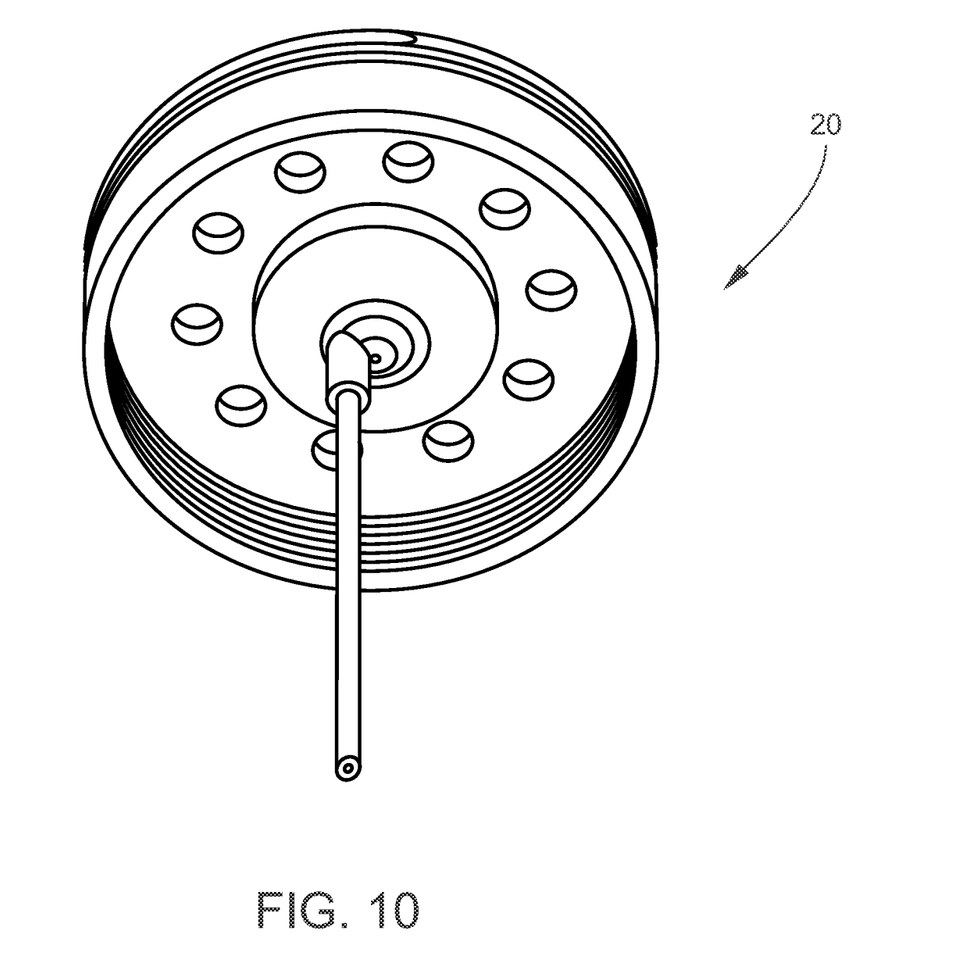

As best shown in FIGS. 3 and 6, the exemplary collector base 21 of collector assembly 20 includes a centrally formed open-end (open access) housing 40 which receives and secures a nozzle 41 of the atomizing device 22. The nozzle housing 40 has a cylindrical upper side wall 42, a reduced-diameter cylindrical lower side wall 43, and an inside annular shoulder 44 located between the upper and lower side walls. An annular mounting disk 46 is integrally-formed with the nozzle 41 of atomizing device 22 and has a marginal edge portion 47 designed to sit against the inside shoulder 44 of the nozzle housing 40. In one embodiment, the mounting disk 46 is disposed substantially perpendicular to a longitudinal axis of the nozzle 41 and is permanently affixed to the inside shoulder 44 by ultrasonic welding, adhesives or other suitable means. The exemplary mounting disk 46 has a protruding annular cartridge-side flange 48 formed adjacent the marginal edge portion 47 and inset from an outside annular edge of the disk 46. The protruding flange 48 closely engages the lower cylindrical side wall 43 of the nozzle housing 40, and functions to properly align the nozzle 41 relative to a source of compressed air (not shown) supplied by the fragrance diffusion system 12. Referring to FIG. 7, the exemplary nozzle 41 may have a tapered nipple 51 with spaced O-rings 52, 53 which cooperate to fluidly seal the connection to the source of compressed air despite any slight misalignment or failure of a single one of the two O-rings. As best shown in FIG. 8, the lower cylindrical side wall 43 may be slightly tapered or "funnel-shaped" to further effect secure and proper placement of atomizing device 22 (and nozzle 41) when assembled with the collector base 21. A perforated collector wall 55 is located inside the collector assembly 20 and extends between and divides the cartridge coupler 23 and the neck 24 of the collector base 21. FIGS. 9 and 10 shown the exemplary collector assembly in an assembled condition.

Referring again to FIGS. 3 and 6, the atomizing device 22 is attached to the collector base 21 as described above, and comprises an internal air passage 61 formed through the nozzle 41 and extending longitudinally from a first open end 62 to a constricted second open end 63. The first open end 62 fluidly connects to the source of compressed air supplied by the fragrance diffusion system 12, while the constricted second end 63 opens into an atomization chamber 65 formed with the collector base 21. The atomization chamber 65 defines a vapor port 66 inline with the air passage 61 through nozzle 41 and communicating with an inside of the fragrance cartridge 10. An end wall 67 of the atomizing device 22 engages the collector base 21 to seal the atomization chamber 65 on an output side of the collector base 21. An elongated vacuum tube 71 comprises a fixed tube section 72 fluidly connected to an inlet 73 of the atomization chamber 65 on a cartridge side of the collector base 21, and a removable extension tube 74 having an open end 75 (FIG. 1) designed to extend into the fragrance oil 11 stored inside the cartridge 10.

Figure 11:
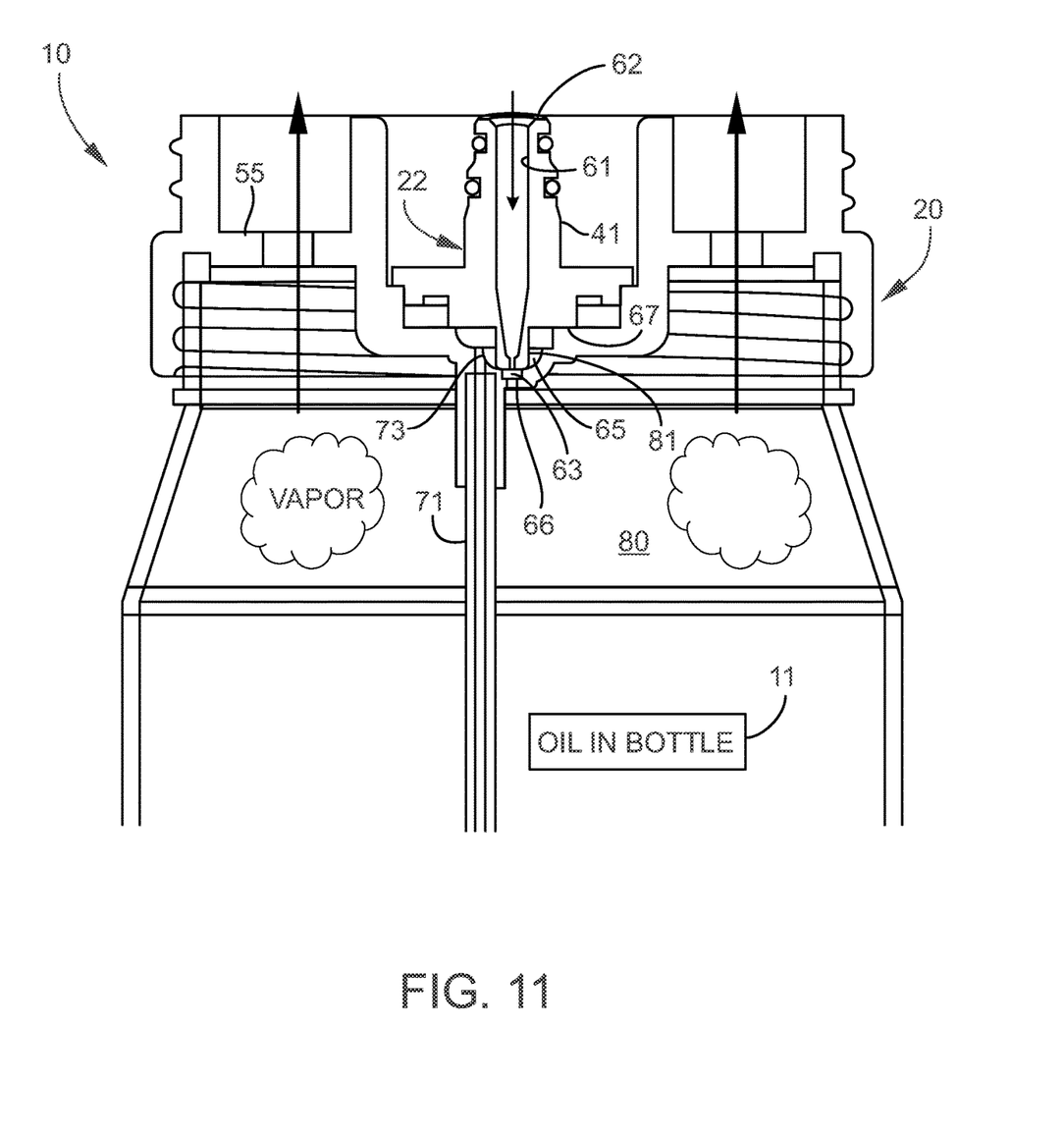
FIG. 11 is a fragmentary cross-sectional view demonstrating operation of the exemplary collector assembly in an exchangeable fragrance cartridge installed in a fragrance diffusion system.

FIG. 11 demonstrates operation of the exemplary collector assembly 20 incorporated in the exchangeable fragrance cartridge 10 and used in combination with the fragrance diffusion system 12 (shown in FIG. 2). The fragrance cartridge 10 is operatively attached to the fragrance diffusion system 12 such that the source of compressed air fluidly connects to the nozzle 41 of atomizing device 22, as previously described. The exemplary fragrance diffusion system 12 commands the source of compressed air to initiate an airblast through the internal passage 61 of the nozzle 41. This command may be initiated either automatically via computer programming or manually on-demand by a user. The resulting airblast through the nozzle 41 of atomizing device 22 creates a suction force (via Bernoulli effect) drawing fragrance oil 11 from the cartridge 10 through the vacuum tube 71 and inlet 73, and into the atomization chamber 65. Inside the atomization chamber 65, the fragrance oil 11 is converted into droplets prior to discharging outwardly through the vapor port 66 and into a vapor chamber 80 inside the cartridge 10. The air passage 61 through the nozzle 41 tapers between the first and second open ends 62, 63, and forms a constricted Venturi tip 81 designed to blast airflow into the atomization chamber 65 and from the atomization chamber 65 through the vapor port 66. The fragrant vapor passes outwardly from the cartridge chamber 80 through the perforated collector wall 55, and may be further directed using a miniature fan (not show) to an output orifice of the fragrance diffusion system 12.

In exemplary embodiments, the present fragrance diffusion system 12 may further comprise a printed circuit board (PCB) box designed to hold circuit components and systems for automatically controlling certain operations of the fragrance diffusion system. Such embodiments may further comprise cloud-based system management allowing users to manage systems and analyze real time data from anywhere in the world.

As described in Applicant's '999 Patent, the PCB box has a PCB box face plate which can be used to provide a mechanism for displaying and/or receiving information for controlling the operation of the fragrance diffusion system. The PCB box face plate may have a glass, plastic, or transparent-like cover to display information regarding a status and controls for the operation of the fragrance diffusion system, and may be able to receive instructions from a user, or be configured with a slot or opening to receive a portable memory card (e.g., a flash memory card) that may contain operational data and/or system settings. The display may be presented, for example, in a liquid crystal display screen (LCD), in which some implementations may be able to have a touch-screen display to receive an input from a user. Some of the information that maybe displayed, for example, may include an estimate of an amount of fragrance oil left in the cartridge bottle, a time period for providing a short burst of fragrance into the air outside of the, and/or a programmable system for delivering the fragrance over an hourly, daily, weekly, monthly, or yearly schedule. For example, the controls for the fragrance diffusion system can be used for cycling the air pump that drives the atomizer on and off. In some implementations, for instance, the control settings can provide at least 50 different combinations of duty cycles and cycle lengths to better suit the desired average amount and timing of fragrance delivery into the air. The controls may also allow for at least 10 periods of fragrance delivery to be scheduled during a calendar week, for example. The occurrences of air delivery can be set as an "event" in the system, which can be associated with settings for the fragrance delivery, including both the duty cycle and the cycle length. The duty cycle can be the amount of time in the cycle length of fragrance delivery. The duty cycle and cycle length can be predetermined or adjusted by the user, for example, based upon the room or the environmental conditions for fragrance delivery. For example, an area with a large space may have a long time for airflow and/or a high speed for the fan to deliver the fragrance into the airspace at a greater rate than would be the case for a small room. The small area, for example, may have short time for airflow and/or a low speed for the fan to deliver the fragrance into the airspace.

Information serving as input into the system may be added by a user of the system, who can program settings using the interface in the PCB box, or the user can download instructions and settings onto the portable memory card and insert the memory card into the system. The user of the system may also refer to a service technician for the system.

The controls can allow for the fan speed to be varied, where the fan speed can be adjusted to be configured to the conditions of the airspace of the room and the noise generated from the fan. For example, a system that is mounted on a high ceiling may have controls configured such that the system has a high fan speed since the fragrance can be forcefully diffused into a large airspace without people noticing the noise generated from the fan. Whereas, the fan speed may be lower in a smaller and/or a quiet room.

Also, the controls can allow for the air pump to be adjusted so that different amounts of air pressure and resulting airflow can be utilized. For example, the air for the air pump can be adjusted to change a rate of diffusion of fragrance oil from the system, and or may be adjusted to allow for different physical characteristics of different fragrance oils to be used with the system. Some implementations of the system also may be able to have detector (not shown) to detect an amount of fragrance that is delivered into an airspace, and may be able to provide feedback to the system such that the airspace is not continuously saturated with the fragrance.

For the purposes of describing and defining the present invention it is noted that the use of relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Exemplary embodiments of the present invention are described above. No element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under 35 U.S.C. § 112(f) [or 6th paragraph/pre-AIA] is not intended. Additionally, it is not intended that the scope of patent protection afforded the present invention be defined by reading into any claim a limitation found herein that does not explicitly appear in the claim itself.

What is claimed:

1. A fragrance cartridge incorporating a collector assembly adapted for use in a fragrance diffusion system, said collector assembly comprising:
    a dual-thread collector base comprising an integrally-formed cartridge coupler and neck, said cartridge coupler having an internal screw thread designed for mating with a complementary external screw thread of said fragrance cartridge, and said neck having an external screw thread matching the internal screw thread of said cartridge coupler, wherein an outside diameter of said neck measured at an outermost thread is equal to an inside diameter of said cartridge coupler measured at a maximum depth of said internal screw thread;
    an atomizing device comprising a flow nozzle attached to said collector base and defining an internal air passage having a first open end adapted for communicating with a source of compressed air and a second open end extending into an atomization chamber formed with said collector base, said atomization chamber defining a vapor port adapted for communicating with an inside of said fragrance cartridge, and said atomizing device further comprising an end wall sealing said atomization chamber on an output side of said collector base;
    an elongated vacuum tube fluidly connected to said atomization chamber on a cartridge side of said collector base, and adapted for extending into a liquid fragrance stored inside said fragrance cartridge, whereby an air-blast through the internal passage of said nozzle creates a suction force drawing liquid fragrance from said cartridge through said vacuum tube and into said atomization chamber where the liquid fragrance is converted into droplets prior to discharging outwardly through said vapor port and into a vapor chamber inside said cartridge; and
    at least one diffusion opening formed in said collector base for enabling movement of fragrant vapor outwardly from said cartridge.

2. The fragrance cartridge according to claim 1, wherein said collector base comprises a centrally formed open-end nozzle housing.

3. The fragrance cartridge according to claim 2, wherein said nozzle housing has a cylindrical upper side wall, a reduced-diameter cylindrical lower side wall adjacent said upper side wall, and an inside annular shoulder located between said upper and lower side walls.

4. The fragrance cartridge according to claim 3, wherein said atomizing device further comprises a mounting disk integrally formed with said nozzle and having a marginal edge portion affixed to said collector base along said annular shoulder of said nozzle housing.

5. The fragrance cartridge according to claim 4, wherein said mounting disk comprises a protruding annular cartridge-side flange.

6. The fragrance cartridge according to claim 5, wherein said lower cylindrical side wall of said nozzle housing is tapered to closely receive said cartridge-side flange of said mounting disk.

7. The fragrance cartridge according to claim 1, and comprising a perforated collector wall located inside said collector base and extending between said cartridge coupler and said neck.

8. The fragrance cartridge according to claim 1, wherein said air passage through said nozzle tapers between said first and second open ends, and forms a constricted Venturi tip designed to blast airflow into said atomization chamber and from said atomization chamber through said vapor port.

9. The fragrance cartridge according to claim 1, wherein said vacuum tube comprises a fixed tube section integrally formed with the cartridge side of said collector base, and an elongated removable extension tube fluidly connected to said fixed tube section.

10. The fragrance cartridge according to claim 1, wherein said nozzle comprises a tapered nipple adapted for fluidly connecting to the source of compressed air.

11. The fragrance cartridge according to claim 10, and comprising first and second spaced apart O-rings located on said tapered nipple and adapted to fluidly seal the connection between said nozzle and the source of compressed air.

12. The fragrance cartridge according to claim 1, wherein said internal and external screw threads of said collector base each comprise at least one continuous turn.

13. The fragrance cartridge according to claim 1, and comprising a removable closure cap having an internal screw thread designed for mating with the external thread of said neck of said collector base, and wherein the internal screw thread of said closure cap matches the internal screw thread of said cartridge coupler.

14. A collector assembly adapted for use in a fragrance diffusion system, said collector assembly comprising:

a dual-thread collector base comprising an integrally-formed cartridge coupler and neck, said cartridge coupler having an internal screw thread designed for mating with a complementary external screw thread of a fragrance cartridge, and said neck having an external screw thread matching the internal screw thread of said cartridge coupler, wherein an outside diameter of said neck measured at an outermost thread is equal to an inside diameter of said cartridge coupler measured at a maximum depth of said internal screw thread;

an atomizing device comprising a flow nozzle attached to said collector base and defining an internal air passage having a first open end adapted for communicating with a source of compressed air and a second open end extending into an atomization chamber formed with said collector base, said atomization chamber defining a vapor port adapted for communicating with an inside of the fragrance cartridge, and said atomizing device further comprising an end wall sealing said atomization chamber on an output side of said collector base;

an elongated vacuum tube fluidly connected to said atomization chamber on a cartridge side of said collector base, and adapted for extending into a liquid fragrance stored inside the fragrance cartridge, whereby an air-blast through the internal passage of said nozzle creates a suction force drawing liquid fragrance from the cartridge through said vacuum tube and into said atomization chamber where the liquid fragrance is converted into droplets prior to discharging outwardly through said vapor port and into a vapor chamber inside the cartridge; and at least one diffusion opening formed in said collector base for enabling movement of fragrant vapor outwardly from the cartridge.

15. The collector assembly according to claim 14, and comprising a perforated collector wall located inside said collector base and extending between said cartridge coupler and said neck.

16. The collector assembly according to claim 14, wherein said air passage through said nozzle tapers between said first and second open ends, and forms a constricted Venturi tip designed to blast airflow into said atomization chamber and from said atomization chamber through said vapor port.

17. The collector assembly according to claim 14, wherein said nozzle comprises a tapered nipple adapted for fluidly connecting to the source of compressed air.

18. The collector assembly according to claim 17, and comprising first and second spaced apart O-rings located on said tapered nipple and adapted to fluidly seal the connection between said nozzle and the source of compressed air.

19. The collector assembly according to claim 14, wherein said internal and external screw threads of said collector base each comprise at least one continuous turn.

20. A fragrance diffusion system incorporating a fragrance cartridge and collector assembly, said collector assembly comprising:

a dual-thread collector base comprising an integrally-formed cartridge coupler and neck, said cartridge coupler having an internal screw thread designed for mating with a complementary external screw thread of said fragrance cartridge, and said neck having an external screw thread matching the internal screw thread of said cartridge coupler, wherein an outside diameter of said neck measured at an outermost thread is equal to an inside diameter of said cartridge coupler measured at a maximum depth of said internal screw thread;

an atomizing device comprising a flow nozzle attached to said collector base and defining an internal air passage having a first open end adapted for communicating with a source of compressed air and a second open end extending into an atomization chamber formed with said collector base, said atomization chamber defining a vapor port adapted for communicating with an inside of said fragrance cartridge, and said atomizing device further comprising an end wall sealing said atomization chamber on an output side of said collector base;

an elongated vacuum tube fluidly connected to said atomization chamber on a cartridge side of said collector base, and adapted for extending into a liquid fragrance stored inside said fragrance cartridge, whereby an air-blast through the internal passage of said nozzle creates a suction force drawing liquid fragrance from said cartridge through said vacuum tube and into said atomization chamber where the liquid fragrance is converted into droplets prior to discharging outwardly through said vapor port and into a vapor chamber inside said cartridge; and at least one diffusion opening formed in said collector base for enabling movement of fragrant vapor outwardly from said cartridge.

* * * * *